United States Patent [19]

Zama et al.

[11] 4,343,732
[45] Aug. 10, 1982

[54] STABILIZED HALOGEN-CONTAINING RESIN COMPOSITIONS

[75] Inventors: Takashi Zama, Kawasaki; Koji Takeuchi, Yokohama; Masuo Yukutomi, Ayase; Fumiyuki Ito, Kawaguchi, all of Japan

[73] Assignee: Ajinomoto Company Incorporated, Tokyo, Japan

[21] Appl. No.: 197,157

[22] Filed: Oct. 15, 1980

[30] Foreign Application Priority Data

Oct. 24, 1979 [JP] Japan .................................. 54/137246

[51] Int. Cl.³ .............................................. C08K 5/52
[52] U.S. Cl. ..................................... 524/114; 524/127
[58] Field of Search ...................... 260/30.6 R, 45.7 P, 260/45.75 W, 45.85 R, 45.95 G, 928, 930

[56] References Cited

U.S. PATENT DOCUMENTS

| | | | |
|---|---|---|---|
| 2,520,090 | 8/1950 | Barrett | 260/930 |
| 3,558,537 | 1/1971 | Hecker et al. | 260/45.75 W |
| 3,869,526 | 3/1975 | Combey et al. | 260/929 |
| 4,123,585 | 10/1978 | Sparzak et al. | 260/30.6 R |

FOREIGN PATENT DOCUMENTS

| | | |
|---|---|---|
| 1215 | 4/1979 | European Pat. Off. |
| 4747 | 10/1979 | European Pat. Off. |
| 680223 | 10/1952 | United Kingdom |
| 734766 | 8/1955 | United Kingdom |
| 734767 | 8/1955 | United Kingdom |
| 743922 | 1/1956 | United Kingdom |
| 745161 | 2/1956 | United Kingdom |
| 1122372 | 8/1968 | United Kingdom |
| 1405983 | 9/1975 | United Kingdom |
| 1424513 | 2/1976 | United Kingdom |
| 1441528 | 7/1976 | United Kingdom |
| 1532904 | 11/1978 | United Kingdom |

*Primary Examiner*—John Kight, III
*Assistant Examiner*—R. A. White
*Attorney, Agent, or Firm*—Oblon, Fisher, Spivak, McClelland & Maier

[57] ABSTRACT

Stabilized halogen-containing resin compositions having improved thermal stability and weather resistance comprising a halogen-containing resin and as a stabilizer, an organic phosphate ester having the general formula:

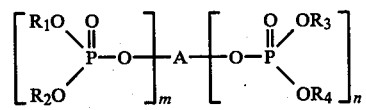

wherein $R_1$ to $R_4$ are the same or different organic radicals, A represents hydrocarbon residue of polyhydric compound having 2 to 6 hydroxyl groups, m and n are each an integer of 1 to 3, and m+n is equal to the total number of hydroxyl groups in polyhydric compound.

3 Claims, No Drawings

STABILIZED HALOGEN-CONTAINING RESIN COMPOSITIONS

The present invention relates to stabilized halogen-containing resin compositions and to novel stabilizers to be incorporated therein. More particularly, the present invention relates to a novel organic phosphate ester which is chemically stable and compatible with a halogen-containing resin and which imparts excellent thermal stability and weather resistance to halogen-containing resins.

It is known that under the action of heat and/or light in the presence of oxygen, the halogen-containing resins undergo numerous changes, namely deteriorations including the formation of carbonyl groups, conjugated double bonds and cross-linkages as well as cleavage of molecular chains, which are accompanied by liberation of hydrogen halide, whereby discolouration and lowering of the mechanical strength are caused.

To prevent or reduce such deterioration, metallic soaps and organo tin stabilizers have been used together with other additives such as antioxidants, ultraviolet absorption agents and stabilizer assistants.

Although stabilizer assistants are commonly used in combination with stabilizers for achieving a synergistic effect in heat and light stabilization of the initial and intermediate periods of time, the heretofore used stabilizer assistants cause undesirable phenomena in heat processability, initial discolouration, physical and chemical properties of the finished product or light stabilization. For example, organic phosphites which have been widely used as stabilizer assistants, such as triphenyl phosphite, tris (nonylphenyl) phosphite, and diphenyl decyl phosphite have disadvantage that they have less favorable long term storage characteristics because they themselves are easily subjected to hydrolysis. In addition, they are less compatible with halogen-containing resins and tend to bleed into surface of resinous sheet when incorporated in large amounts. The commonly used organic phosphates, such as tricresyl phosphate and trixylenyl phosphate, are inferior in heat stability and weather resistance.

An object of the present invention is to provide a novel stabilizer for halogen-containing resins which is free from such disadvantages as observed in the organic phosphites and organic phosphates heretofore used as stabilizer assistants.

An another object of the present invention is to provide a novel organic phosphate ester which is chemically stable during long-term storage and compatible with halogen-containing resins and which has an improved stabilizing effect against the deterioration of halogen-containing resins.

A further object of the present invention is to provide stabilized halogen-containing resin compositions having improved thermal stability and weather resistance.

It has been found that a specific organo phosphorous compound, wherein two or more of hydroxyl groups in a polyhydric compound form an ester with phosphoric acid, is a satisfactory stabilizer for halogen-containing resins.

According to the present invention, there are provide halogen-containing resin compositions comprising a halogen-containing resin and as a stabilizer an organic phosphate ester having the general formula:

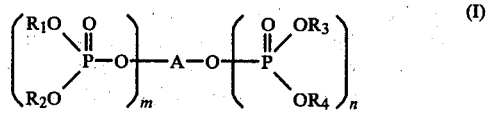

wherein $R_1$ to $R_4$ are the same or different organic radicals selected from the group consisting of alkyl, alkenyl, cycloalkyl, aryl, alkoxyalkyl, acyloxyalkyl, polyoxyalkylenealkyl, polyoxyalkylenearyl, alkyl substituted aryl and arylalkyl radicals, A is hydrocarbon residue of polyhydric compound having 2 to 6 hydroxyl groups in the molecules, said polyhydric compound being selected from the group consisting of polyhydric alcohol, polyhydric phenol and polyoxyalkylene glycol, m and n are each integer of 1 to 3 and m+n is equal to the total number of hydroxyl groups in the polyhydric compound.

Examples of halogen-containing resins which may be stabilized with the organic phosphate ester of the general formula (I) in the present invention include polyvinyl halide; polyvinylidene halide; a copolymer of vinyl halide and vinylidene halide; a copolymer of vinyl halide and ethylene; a copolymer of vinyl halide or vinylidene halide with another unsaturated monomer copolymerizable therewith, for example the vinyl esters of carboxylic acids such as vinyl acetate, vinyl propionate, vinyl butyrate and vinyl benzoate; esters of unsaturated acids such as methyl, ethyl, propyl, butyl and allyl esters of acrylic acid and the corresponding esters of methacrylic acid; vinyl aromatic compounds such as styrene; esters of $\alpha,\beta$-unsaturated carboxylic acids such as methyl, ethyl, propyl and octyl esters of maleic, crotonic, itaconic and fumaric acids; halogenated polyolefins e.g. chlorinated polyethylene and chlorinated polypropylene; and polyolefins containing a very small amount of halogenide catalyst as impurity. Preferably the halides referred to in this present paragraph are chlorides.

In the organic phosphate ester represented by the general formula (I) which is a valuable stabilizer in the present invention, $R_1$, $R_2$, $R_3$ and $R_4$ may be identical or different organic hydrocarbon radical or organic hydrocarbon radical containing ether linkage. Representative examples of such organic radicals are the following:

$C_{4-18}$alkyl radicals such as butyl, isobutyl, t-butyl, pentyl, isopentyl, hexyl, octyl, 2-ethylhexyl, isooctyl, nonyl, decyl, dodecyl, tridecyl, hexadecyl and octadecyl; $C_{4-18}$alkenyl radicals such as hexenyl, dodecenyl and oleoyl; $C_{5-8}$cycloalkyl radicals such as cyclopentyl and cyclohexyl; aryl radicals such as phenyl and naphthyl; $C_{3-20}$alkoxyl or $C_{8-20}$cycloalkoxyalkyl radicals such as methoxyethyl, ethoxyethyl, propoxyethyl, isopropoxyethyl, butoxyethyl, isobutoxyethyl, t-butoxyethyl, amyloxyethyl, hexoxyethyl, cyclohexoxyethyl, heptoxyethyl, octoxyethyl, 2-ethylhexoxyethyl, decyloxyethyl, dodecyloxyethyl, methoxypropyl, ethoxypropyl, butoxypropyl, t-butoxypropyl, cyclohexoxypropyl, octoxypropyl, methoxybutyl, 3-methoxybutyl, butoxybutyl, t-butoxybutyl, cyclohexoxybutyl, octoxybutyl and 2-ethylhexoxybutyl; alkoxycycloalkyl radicals such as methoxycyclohexyl, ethoxycyclohexyl, butoxycyclohexyl, t-butoxycyclohexyl and t-butoxycyclohexyl; aryloxyalkyl radicals such as phenoxyethyl and phenoxybutyl; aryl alkoxyalkyl radicals such as benzyloxyethyl, and benzyloxybutyl; alkoxy substituted aryl radicals such as methoxyphenyl, ethoxyphenyl, propoxyphenyl, isopropoxyphenyl, butoxyphenyl, isobutoxyphenyl, t-butoxyphenyl, hexoxyphenyl, cyclohexoxyphenyl, octoxyphenyl and 2-ethylhexoxyphenyl; alkyl substituted aryl radicals such as cresyl, xylyl, ethylphenyl, propylphenyl, isopropylphenyl, butylphenyl, isobutylphenyl, t-butylphenyl, isoamylphenyl, hexylphenyl, cyclohexylphenyl, octylphenyl, 2-ethylhexylphenyl, nonylphnyl, decylphenyl, p-cumylphenyl, 2,6-di-t-butylphenyl and 2,6-di-t-butyl-4-methylphenyl; arylalkyl radicals such as benzyl, 2-methylbenzyl, phenylethyl, phenylpropyl, phenylisopropyl, phenylbutyl, phenylisobutyl, phenyl-t-butyl and phenylcyclohexyl; alkyl substituted arylalkyl radicals such as methylbenzyl, ethylbenzyl, propylbenzyl, isopropylbenzyl, butylbenzyl, isobutylbenzyl, t-butylbenzyl, cyclohexylbenzyl, methyl phenyl ethyl, isopropyl phenyl ethyl, methyl phenyl isopropyl, ethyl phenyl isopropyl and t-butyl phenyl isopropyl; and residues derived from ether linkage containing compounds such as diethylene glycol monomethyl ether, diethylene glycol monopropyl ether, diethylene glycol monoisopropyl ether, diethylene glycol monobutyl ether, diethylene glycol mono t-butyl ether, diethylene glycol monocyclohexyl ether, diethylene glycol monoisobutyl ether, diethylene glycol monooctyl ether, diethylene glycol mono-2-ethylhexyl ether, diethylene glycol monononyl ether, diethylene glycol monodecyl ether, diethylene glycol monododecyl ether, diethylene glycol monophenyl ether, diethylene glycol monophenylethyl ether, diethylene glycol monoethylbenzyl ether, diethylene glycol monoisopropylbenzyl ether, diethylene glycol monophenylisopropyl ether, triethylene glycol monomethyl ether, triethylene glycol monoethyl ether, triethylene glycol monobutyl ether, triethylene glycol monooctyl ether, triethylene glycol mono-2-ethylhexyl ether, triethylene glycol monocyclohexyl ether, triethylene glycol monobenzyl ether, triethylene glycol monophenyl ether, dipropylene glycol monoethyl ether, dipropylene glycol monobutyl ether, dipropylene glycol monocyclohexyl ether, dipropylene glycol monobenzyl ether, dipropylene glycol monophenyl ether, dibutylene glycol monomethyl ether, dibutylene glycol monoethyl ether, dibutylene glycol monobutyl ether and dibutylene glycol monophenyl ether.

The hydrocarbon residues of polyhydric compounds represented by A in the general formula (I) are those resulting from the reaction of all of the hydroxyl groups from polyhydric compounds having 2 to 6 hydroxyl groups. Examples of polyhydric compounds include polyhydric alcohols such as ethylene glycol, propylene glycol, isopropylene glycol, butylene glycol, isobutylene glycol, pentylene glycol, hexylene glycol, cyclohexylene glycol, isopentylene glycol, heptylene glycol, octylene glycol, isoocytylene glycol, neopentylene glycol, 1,3,5-trihydroxypentane, trimethylol propane, glycerin and pentaerythritol; polyhydric phenol such as bisphenol A, 2,2'-bis(4-hydroxy-8-t-butylphenyl) propane, methylenebis(p-cresol), methylenebis(2,6-di-t-butylphenol), 4,4'-thiobisphenol and 4,4'-thiobis(4-methyl-6-t-butylphenol); and polyoxyalkylene glycols such as dioxyethylene glycol, trioxyethylene glycol, tetraoxyethylene glycol, dioxypropylene glycol and trioxypropylene glycol.

Also, each of m and n in the general formula (I) is an integer 1 to 3, and depends on number of hydroxyl groups in a polyhydric compound employed. An organic phosphate ester wherein each of m and n is 1 is the most general.

In the preparation of an organic phosphate ester of the present invention, there are preferably employed as raw materials a polyhydric compound corresponding to A, a monohydric compound corresponding to $R_1$ to $R_4$ and phosphorous oxychloride.

In one preferred process, a polyhydric compound is reacted with phosphorous oxychloride in such relative amount as to provide 0.8 to 1.2 equivalent weight of polyhydric compound per mole of phosphorous oxychloride at an elevated temperature of 70° C. to 110° C. in the presence of 0.2 to 2.0 by weight % of a Friedel-Crafts reaction catalyst (e.g. aluminum chloride, zinc chloride or boron trifluoride etherate) based on the polyhydric compound. After hydrogen chloride has been evoluted, subsequently resultant reaction mixture is mixed with 2.0 to 2.4 times moles of a monohydric compound based on the phosphorous oxychloride employed initially and heated at an elevated temperature of 100° C. to 200° C. until evolution of hydrogen chloride ceases.

Inert solvents such as toluene and xylene may be employed, if desired.

After the completion of the reaction, catalyst is removed from the reaction mixture by the conventional procedure, for example by washing with water. Thereafter, the reaction mixture is distilled under reduced pressure to remove excess reactants and solvent, if any, and then filtered to remove a small amount of insoluble material and to obtain the desired organic phosphate ester which is a colourless or pale yellowish viscous liquid.

The equivalent weight of a polyhydric compound is its molecular weight divided by number of hydroxyl group.

In another process, the organic phosphate ester of the present invention may be prepared in one step by adding phosphorous oxychloride to a mixture of a polyhydric compound, a monohydric compound and a catalyst and heating at an elevated temperature of 60° C. to 200° C. until evolution of hydrogen chloride ceases.

The preferred organic phosphate esters of the present invention are ones derived from a dihydric compound, a monohydric compound and phosphorous oxychloride. Representative dihydric compounds are bisphenol A, 1,6-hexanediol and ethylene glycol. And, representative monohydric compounds are phenol, $C_{1-10}$alkyl substituted phenol and $C_{4-18}$ aliphatic alcohol.

Furthermore, the organic phosphate ester of the present invention may be prepared by reacting an organo phosphorochloridate corresponding to $R_1$, $R_2$, $R_3$ and $R_4$ with a polyhydric compound in an aromatic hydrocarbon solvent such as benzene or toluene in the presence of a tertiary amine such as triethylamine which is capable of binding hydrochloric acid formed during the reaction.

The organic phosphate ester of the general formula (I) which may be used as stabilizer in the present invention may be one prepared by any process. Purified organic phosphate ester is most preferred for use as stabilizer but it is not necessarily to employ purified (I). Crude (I) or the reaction mixture containing the organic phosphate ester of the general formula (I) may be conveniently employed.

The amount used of organic phosphate ester of the present invention may be 0.01 to 10 parts by weight, preferably 0.1 to 5 parts, based on 100 parts by weight of halogen-containing resins. Also, the organic phosphate ester of the present invention may be employed in combination with other known stabilizers, stabilizer assistants, anti-oxidants and ultraviolet absorption agents.

As the known stabilizers, there are metal salts of fatty acid such as Zn, Ca, Ba, Mg and Sn salts, organo tin mercaptides and organo tin mercaptoacid ester. Especially, Ca-Zn salt or Ba-Zn salt of fatty acid having 6 to 22 carbon atoms gives superior heat stability, discolouration preventing property and weather resistance when employed together with the organic phosphate ester of the present invention than when employed together with the known organic phosphites or organic phosphates.

Examples of the known stabilizer assistants which may be preferably employed together with the organic phosphate ester of the present invention include liquid epoxy compounds, organic phosphites, organic phosphates and polyhydric alcohols.

Furthermore, the organic phosphate ester of the present invention may be employed in combination with other commonly used additives such as lubricants, fillers and plasticizers.

The organic phosphate esters of the present invention are highly valuable stabilizers for halogen-containing resins in practical use from the following aspects.

(1) They withstand long-term storage owing to their chemical stability, unlike the commonly used organic phosphites.

(2) They are completely compatible with halogen-containing resins and cause little or no bleeding phenomenon into surface of film even when employed in large amount.

(3) They are superior with respect to the initial and intermediate thermal stability and weather resistance in comparison with the known organic phosphates, and correspondingly the amount added of the stabilizer may be decreased for purpose of achieving the same level of stabilization effect as the known organic phosphates.

The following examples 1 to 4 serve to illustrate the preparation of the novel organic phosphate esters of the present invention, but are not be considered as limiting with respect thereto.

EXAMPLE 1

22.8 Grams (0.1 M) of bisphenol A was mixed with 0.3 g of powdery aluminum chloride and then heated to 80°–90° C. 30.7 Grams (0.2 M) of phosphorus oxychloride was dropwise added thereto over a period of 1 hour. Thereafter, 45.4 g (0.42 M) of cresol was added dropwise over a period of 1 hour. The temperature was raised at a rate of 10° C./30 minutes until it reached 180° C. After cooling, viscous reaction solution was diluted with 200 ml of toluene and washed twice with 200 ml of water to remove aluminum chloride catalyst. Toluene solvent was removed by distillation under reduced pressure and the residue was filtered out to obtain compound No. 1 shown in table 1.

| Phosphorous content | Calculated | 8.28% |
|---|---|---|
| | Found | 8.10% |
| Yield: 98% | | |
| Appearance: colourless liquid | | |

EXAMPLE 2

22.8 Grams (0.1 M) of bisphenol A was sufficiently mixed with 0.3 g of powdery aluminum chloride and the mixture was heated at 80°–90° C. 30.7 Grams (0.2 M) of phosphorus oxychloride was added dropwise over a period of 1 hour and 54.7 g (0.42 M) 2-ethyl hexanol was added dropwise over a period of 1 hour. Thereafter, the temperature was raised at a rate of 10° C./1 hour until it reached 140° C. After cooling, the reaction mixture was dissolved in 200 ml of toluene and washed twice with 200 ml of water to remove aluminum chloride catalyst. Excess 2-ethylhexanol was removed by distillation under reduced pressure and the residue was filtered to obtain compound No. 4 shown in table 1.

| Phosphorous content | Calculated | 7.41% |
|---|---|---|
| | Found | 7.49% |
| Yield: 96% | | |
| Appearance: colorless liquid | | |

EXAMPLE 3

A mixture of 11.8 g (0.1 M) 1.6-hexanediol, 54.7 g (0.42 M) n-octylalcohol and 0.3 g powdery aluminum chloride was heated at 80° C. 30.7 Grams (0.2 M) phosphorus oxychloride was added dropwise over a period of 1 hour and then the temperature was raised at a rate of 10° C./30 minutes until it reached 150° C. After cooling, the reaction mixture was dissolved in 200 ml toluene and washed twice with 200 ml water to remove aluminum chloride catalyst. The reaction mixture was distilled under reduced pressure to remove toluene and excess n-octylalcohol and filtered to obtain compound No. 5 shown in table 1.

| Phosphorous content | Calculated | 8.53% |
|---|---|---|
| | Found | 8.33% |
| Yield: | 96% | |
| Appearance: colorless liquid | | |

EXAMPLE 4

Other organic phosphate esters were prepared according to the similar procedures as in preceding examples 1–3 and the results are in table 1.

TABLE 1

| No. | Stabilizer | Phosphorous content Calculated | Found | Appearance | Yield % |
|---|---|---|---|---|---|
| 1 | Bis-phosphate of bisphenol A with di(p-tolyl) groups (see structure) | 8.28% | 8.10% | Colorless liquid | 98 |
| 2 | Bis-phosphate of bisphenol A with diphenyl groups | 8.95 | 8.90 | Colorless liquid | 97 |
| 3 | Bis-phosphate of bisphenol A with di(p-isopropylphenyl) groups | 7.20 | 7.21 | Colorless liquid | 98 |
| 4 | Bis-phosphate of bisphenol A with di-$C_8H_{17}$ groups | 7.41 | 7.49 | Colorless liquid | 96 |
| 5 | Bis-phosphate of 1,6-hexanediol with di-$C_8H_{17}$ groups | 8.53% | 8.33% | Colorless liquid | 96 |
| 6 | Bis-phosphate of 1,6-hexanediol with di(p-tolyl) groups | 9.71 | 9.50 | Colorless liquid | 97 |

Structures:

1. $O=P(O\text{-}p\text{-}C_6H_4\text{-}CH_3)_2\text{-}O\text{-}C_6H_4\text{-}C(CH_3)_2\text{-}C_6H_4\text{-}O\text{-}P(O\text{-}p\text{-}C_6H_4\text{-}CH_3)_2=O$ 2. $O=P(OC_6H_5)_2\text{-}O\text{-}C_6H_4\text{-}C(CH_3)_2\text{-}C_6H_4\text{-}O\text{-}P(OC_6H_5)_2=O$ 3. $O=P(O\text{-}p\text{-}C_6H_4\text{-}CH(CH_3)_2)_2\text{-}O\text{-}C_6H_4\text{-}C(CH_3)_2\text{-}C_6H_4\text{-}O\text{-}P(O\text{-}p\text{-}C_6H_4\text{-}CH(CH_3)_2)_2=O$ 4. $O=P(O\text{-}C_8H_{17})_2\text{-}O\text{-}C_6H_4\text{-}C(CH_3)_2\text{-}C_6H_4\text{-}O\text{-}P(O\text{-}C_8H_{17})_2=O$ 5. $O=P(O\text{-}C_8H_{17})_2\text{-}O\text{-}CH_2CH_2CH_2CH_2CH_2CH_2\text{-}O\text{-}P(O\text{-}C_8H_{17})_2=O$ 6. $O=P(O\text{-}p\text{-}C_6H_4\text{-}CH_3)_2\text{-}O\text{-}CH_2CH_2CH_2CH_2CH_2CH_2\text{-}O\text{-}P(O\text{-}p\text{-}C_6H_4\text{-}CH_3)_2=O$ TABLE 1-continued
| No. | Stabilizer | Phosphorous content Calculated | Found | Appearance | Yield % |
|---|---|---|---|---|---|
| 7 | 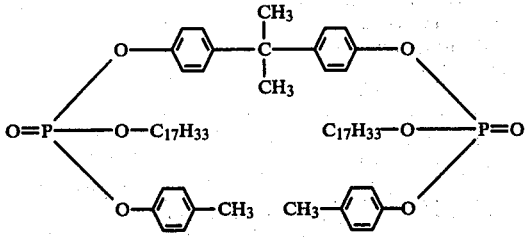 | 5.96 | 5.85 | Pale yellowish liquid | 95 |
| 8 | 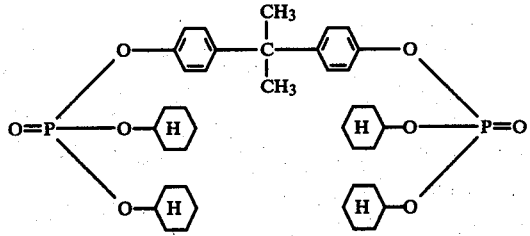 | 8.61 | 8.51 | Pale yellowish liquid | 96 |
| 9 | 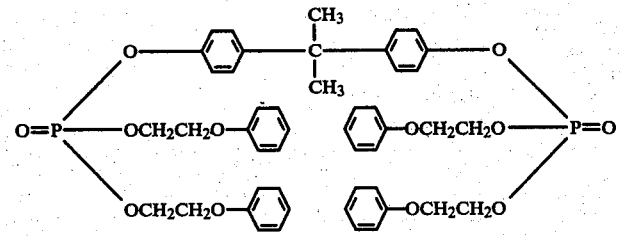 | 7.14 | 7.01 | Pale yellowish liquid | 98 |
| 10 | 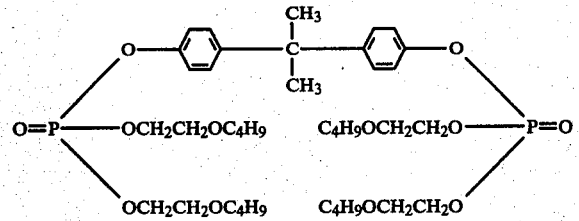 | 7.86% | 7.81% | Pale yellowish liquid | 95 |
| 11 | 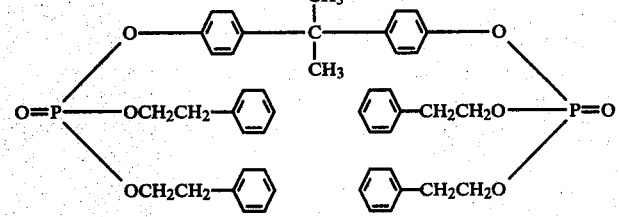 | 7.71 | 7.70 | Pale yellowish liquid | 96 |
| 12 | 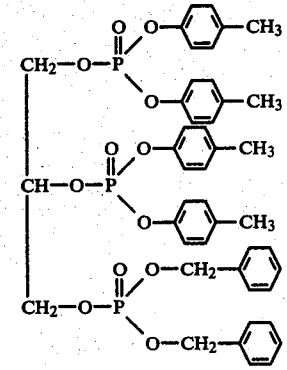 | 10.65 | 10.40 | Pale yellowish liquid | 92 |

The following examples 5 to 8 illustrate the stabilizing action of the organic phosphate esters of the present invention. All parts referred to in examples are by weight.

EXAMPLE 5

To 100 parts polyvinyl chloride having a degree of polymerization of 1300, were added 45 parts dioctylphthalate, 1 part liquid epoxy resin "Epon #828" (trade name, a product of Shell Chem Co. Inc. diglycidyl ether of bisphenol A), 1.2 part zinc stearate, 0.8 part calcium stearate and 2 parts compound shown in table 1, and mixed throughly. The mixture was blended for 5 minutes on a two-roll mill heated to 160° C. and having a roll diameter of 6 inch and rolled into films having a thickness of 0.2 mm. Each film was subjected to heat treatment in a Geer's aging tester maintained to 190° C. and the number of minutes of heat treatment required for the films to turn black was examined for evaluation of thermal stability. Also, other films which had not been subjected to heat treatment were blended for 5 minutes with the two-roll mill heated to 175° C. and rolled into films having 0.15 mm thickness, which were tested for evaluation of weather resistance with a sunshine weather tester. Weather resistance was evaluated by treatment time at that time sample became black or brittle.

For comparison, a similar test was conducted with the known organic phosphates (tricresyl phosphate and trixylenyl phosphate) and organic phosphates (triphenyl phosphite and tris (nonylphenyl) phosphite).

The results obtained are shown in table 2.

TABLE 2

| Additive, part | Thermal stability (minute) | Weather resistance (hour) |
| --- | --- | --- |
| Tricresyl phosphate | 5.0 | 40 | 1000 |
| Trixylenyl phosphate | 5.0 | 40 | 1000 |
| Triphenyl phosphite | 1.0 | 40 | 1100 |
| Tris(nonylphenyl) phosphite | 1.0 | 35 | 900 |
| Compound No. 1 | 2.0 | 45 | 1500 |
| Compound No. 3 | 2.0 | 45 | 1500 |
| Compound No. 7 | 2.0 | 45 | 1500 |
| Compound No. 8 | 2.0 | 45 | 1500 |
| Compound No. 9 | 2.0 | 45 | 1500 |

EXAMPLE 6

To 100 parts polyvinyl chloride having a degree of polymerization of 1100, were added 30 parts dioctyl phthalate, 2 parts epoxidized soybean oil, 1.2 part zinc stearate, 0.8 part barium stearate and 2 parts compounds shown in Table 1, and mixed throughly.

The mixture was blended for 5 minutes on a two-6 inch roll mill heated to 160° C. and rolled into films having 0.2 mm thickness. These films were divided into two groups. One group of films was subjected to heat treatment in a Geer's aging tester heated to 180° C. for evaluation of thermal stability.

Also, another group of films was blended for 5 minutes on a two-6 inch roll mill heated to 175° C. and rolled into films having 0.15 mm thickness, which were subjected to bleeding test.

The results obtained are shown in table 3.

TABLE 3

| Additive (2 parts) | Thermal stability (minutes) | Bleeding property* |
| --- | --- | --- |
| Tricresyl phosphate | 90 | Little |
| Triphenyl phosphite | 100 | Very much |
| Tris(nonylphenyl) phosphite | 100 | Much |
| Compound No. 2 | 110 | Little |
| Compound No. 4 | 110 | Little |
| Compound No. 5 | 110 | Little |
| Compound No. 6 | 110 | Little |
| Compound No. 12 | 110 | Little |

*Ten films, each film having 0.15 mm thickness, were piled each other and examined after three months storage at room temperature for evidence of bleeding or white spots appearing therein.

EXAMPLE 7

The following ingredients were mixed throughly, dried, blended for 5 minutes on a two-6 inch roll mill heated to 170° C. and rolled into sheets having 0.5 mm thickness. These sheets were further rolled into films having 0.2 mm thickness with a two-8 inch roll mill heated to 185° C. One group of films was placed in a Geer's aging tester heated to 180° C. for evaluation of thermal stability. Also, another group of films was subjected to exposure to outdoor spontaneous conditions for evaluation of weather resistance.

The obtained results are shown in table 4.

| Formulation | Parts |
| --- | --- |
| Polyvinyl chloride (D.P. of 1300) | 100 |
| Dioctyl phthalate | 3 |
| Epoxidized soybean oil | 5 |
| Zinc stearate | 0.6 |
| Calcium stearate | 0.4 |
| Organic phosphate | 2.0 |

TABLE 4

| Additive | Thermal stability, blackening time (min.) | Weather-resistance (number of month causing deterioration) |
| --- | --- | --- |
| None (control) | 30 | 6 |
| Compound No. 1 | 40 | 12 |
| Compound No. 3 | 40 | 12 |
| Compound No. 8 | 45 | 12 |
| Compound No. 11 | 40 | 12 |

EXAMPLE 8

To 100 parts polyvinyl chloride having a degree of polymerization of 1300, were added 45 parts dioctyl phthalate, 1.0 part bisphenol-glycidyl ether type of epoxy resin ("Epon #828" trade name, a product of Shell Chem Co., Inc.), 0.7 part zinc stearate, 0.3 part barium stearate, 1.0 part organic phosphite "KH-400C-Z" (trade name, a product of Kyodo Chemical Co., Ltd.), 1.5 part sorbitan monopalmitate and 2.0 parts organic phosphate, and then mixed throughly. The mixture was blended for 5 minutes on a two-6 inch roll mill heated to 160° C. and rolled into films having 0.2 mm thickness, which were further rolled into films having 0.1 mm thickness with two-8 inch roll mill heated to 180° C. for bleeding test and exposure test to outdoor.

These test results are shown in table 5.

TABLE 5

| Additive | Bleeding property* | Weather resistance** |
| --- | --- | --- |
| None (control) | Little | 6 |
| Tricresylphosphate (control) | Little | 10 |
| Compound No. 1 | Little | 16 |
| Compound No. 6 | Little | 15 |
| Compound No. 9 | Little | 18 |
| Compound No. 10 | Little | 18 |

*Ten films were piled together and examined after 6 month-storage at room temperature with respect to white spots appearing therein.

**Number of month required for sample to turn black or to become brittle.

What we claim is:

1. A stabilized composition, comprising:

a halogen-containing resin;

an organic phosphate ester having the formula:

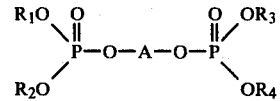

wherein $R_1$, $R_2$, $R_3$, and $R_4$ independently represent a phenyl, $C_1$ to $C_{10}$ alkyl-substituted phenyl, cyclohexyl, phenoxyethyl, or phenylethyl radical and A is the hydrocarbon residue of bisphenol A; and a calcium-zinc or barium-zinc salt of a $C_6$ to $C_{22}$ fatty acid, wherein said organic phosphate ester is present in an amount of from 0.01 to 10 parts by weight per 100 parts by weight of said halogen-containing resin.

2. The composition of claim 1, wherein said halogen-containing resin is polyvinyl chloride, polyvinylidene chloride, a copolymer of vinyl chloride or vinylidene chloride with a copolymerisable unsaturated monomer, a chlorinated polyethylene, or a chlorinated polypropylene.

3. The composition of claim 1, wherein said composition further comprises a liquid epoxy compound as a stabilizer assistant.

* * * * *